US007585672B2

(12) United States Patent
Odorico et al.

(10) Patent No.: US 7,585,672 B2
(45) Date of Patent: Sep. 8, 2009

(54) DIFFERENTIATION OF STEM CELLS TO ENDODERM AND PANCREATIC LINEAGE

(75) Inventors: Jon Odorico, Madison, WI (US); Brenda Kahan, Madison, WI (US); Nathan Treff, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/094,902

(22) Filed: Mar. 31, 2005

(65) Prior Publication Data

US 2005/0260749 A1 Nov. 24, 2005

Related U.S. Application Data

(60) Provisional application No. 60/559,209, filed on Apr. 1, 2004.

(51) Int. Cl.
*C12N 5/08* (2006.01)
(52) U.S. Cl. .................................................. 435/366
(58) Field of Classification Search ....................... None
See application file for complete search history.

(56) References Cited

U.S. PATENT DOCUMENTS

| 7,033,831 | B2 * | 4/2006 | Fisk et al. .................... 435/377 |
| 2003/0138949 | A1 | 7/2003 | Bhushan et al. |
| 2003/0194802 | A1 * | 10/2003 | Itskovitz-Eldor et al. ..... 435/366 |

FOREIGN PATENT DOCUMENTS

| WO | WO01/62899 | * | 8/2001 |
| WO | WO 03/040355 A1 | * | 5/2003 |
| WO | WO/03/050249 | | 6/2003 |

OTHER PUBLICATIONS

Levenberg, S et al PNAS USA 2002;99:4391-96.*
Bhushan et al. (Development 201; 128: 5109-5117).*
Henderson et al. (Stem Cells. 2002; 20: 329-337).*
Balzar et al. ( J Mol Med. 1999; 77: 699-712).*
Andrews (Phil. Trans. R. Soc. Lond. 2002; 357(B): 405-417).*
Assady, S., et al., "Insulin Production by Human Embryonic Stem Cells," Diabetes 50:1691-1697 (2001).
Bhushan, A., et al., "Fgf10 is essential for maintaining the proliferative capacity of epithelial progenitor cell . . . ," Development 128:5109-5117 (2001).
Blyszczuk, P., et al., "Expression of Pax4 in embryonic stem cells promotes differentiation of nestin-positive porgenitor . . . ," PNAS 100:998-1003 (2003).
Colman, A., "Making new beta cells from stem cells," Seminars in Cell & Developmental Biology 15:337-345 (2004).
Gertow, K., et al., "Organized Development from Human Embryonic Stem Cells After Injection into Immunodeficient Mice," Stem Cells and Development 13:421-435 (2004).
Hansson, M., et al., "Artifactual Insulin Release From Differentiated Embryonic Stem Cells," Diabetes 53:2603-2609 (2004).
Hori, Y., et al., "Growth inhibitors promote differentiation of insulin-producing tissue from embryonic stem cells," PNAS 99:16105-16110 (2002).
Houard, N., et al., "HNF-6-independent differentiation of mouse embryonic stem cells into insulin-producing cells," Diabetologia 46:378-385 (2003).
Kahan, B.W., et al., "Pancreatic Precursors and Differentiated Islet Cell Types From Murine Embryonic Stem Cells," Diabetes 52:1-9 (2003).
Kim, D., et al., "in Vivo Functioning and Transplantable Mature Pancreatic Islet-Like Cell Clusters Differentiated from Embryonic Stem Cell," Pancreas 27:e34-e41 (2003).
Ku, H.T., et al, "Committing Embryonic Stem Cells to Early Endocrine Pancreas In Vitro," Stem Cells 22:1205-1217 (2004).
Kubo, A., et al., "Development of definitive endoderm form embryonic stem cells In culture," Development 131:1651-1662 (2004).
Lumelsky, N., et al., "Differentiation of Embryonic Stem Cells to Insulin-Secreting Structures Similar to Pancreatic Islets," Science 292:1389-1394 (2001).
Lundblad, J.R.,et al., "Fluorescence Polarization Analysis of Protein-DNA and Protein-Protein Interactions," Molecular Endocrinology 10:607-612 (1996).
Milne, H.M., et al., "Generation of insulin-expressing cells from mouse embryonic stem cells," Biochemical and Biophysical Research Communications, 328:399-403 (2005).
Miyazaki, S., et al., "Regulated Expression of pdx-1 Promotes In Vitro Differentiation of Insulin-Producing Cells From Embryonic Stem Cells," Diabetes 53:1030-1037 (2004).
Moritoh, Y., et al., "Analysis of Insulin-Producing Cells During In Vitro Differentiation From Feeder-Free Embryonic Stem Cells," Diabetes 52:1163-1168 (2003).
Nasir, M.S., et al, "Fluorescence polarization: an analytical tool for Immunoassay and drug discovery," Abstract Comb Chem High Throughput Screen Aug 2:177-190 (1999).
Rajagopal, J., et al., Insulin Staining of ES Cell Progeny from Insulin Uptake, Science 299:363 (2003).
Segev, H., et al., "Differentiation of Human Embryonic Stem Cells into Insulin-Producing Clusters," Stem Cells 22:265-274 (2004).
Shiroi, A., et al., "Identification of Insulin-Producing Cells Derived from Embryonic Stem Cells by Zinc-Chelating Dithizone," Stem Cells 20:284-292 (2002).
Siplone, S., et al.,"Insulin expressing cells from differentiated embryonic stem cells are not beta cells," Diabetologia 47:499-508 (2004).
Skoudy, A., et al., "TGFBeta, FGF and retinoid signalling pathways promote pancreatic exocrine gene expression . . . ," Biochemical Journal Immediate Publication Manuscript BJ20031784 (2004).

(Continued)

*Primary Examiner*—Janet L Epps-Smith
*Assistant Examiner*—Scott Long
(74) *Attorney, Agent, or Firm*—Quarles & Brady LLP

(57) ABSTRACT

Methods are described to increase the proportion of endoderm committed cells and pancreatic lineage cells in a culture of human embryonic stem cells which are undergoing differentiation. The method also results in a stem cell derived cell culture which does not have tumorigenic capability.

7 Claims, 7 Drawing Sheets

OTHER PUBLICATIONS

Soria, B., et al., "Insulin-Secreting Cells Derived From Embryonic Stem Cells Normalize Glycemia in Streptozotocin-Induced Diabetic Mice," Diabetes 48:1-6 (2000).

Vetere, A., et al., "Neurogenin3 triggers Beta-cell differentiation of retinoic acid-derived endoderm cells," Biochem. J. 371-831-841 (2003).

Carson, C.T., et al., "Stem Cells: The Good, Bad and Barely in Control," Nature Medicine 12:1237-1238 (2006).

Roy, N.S., et al., "Functional engraftment of human ES cell-derived dopaminergic neurons enriched by coculture . . . ," Nature Medicine 12:1259-1268 (2006).

Hentze, H., et al., "Cell therapy and the safety of embyronic stem cell-derived grafts," Trends in Biotechnology 25:24-32 (2006).

Jiang, J., et al., "Generation of Insulin-producing Islet-like Clusters from Human Embryonic Stem Cells," Stem Cells published online May 17, 2007 (1-22).

* cited by examiner

| B) Cell inoculum | Cell Dose | Fraction of inoculations resulting in teratomas* |
|---|---|---|
| EpCAM +, SSEA3-, SSEA1- | $1 \times 10^6$ | 0/5 |
| EpCAM -, SSEA3-, SSEA1- | $1 \times 10^6$ | 2/7 |
| EpCAM -, SSEA3-, SSEA1- | $2 \times 10^6$ | 1/6 |
| Unsorted | $1 \times 10^6$ | 2/3 |
| Unsorted | $2 \times 10^6$ | 7/7 |

* defined as a mass >3mm after 6 weeks of *in vivo* growth

ENRICHMENT OF ISLET PRECURSORS FROM MURINE ES CELLS USING MACS

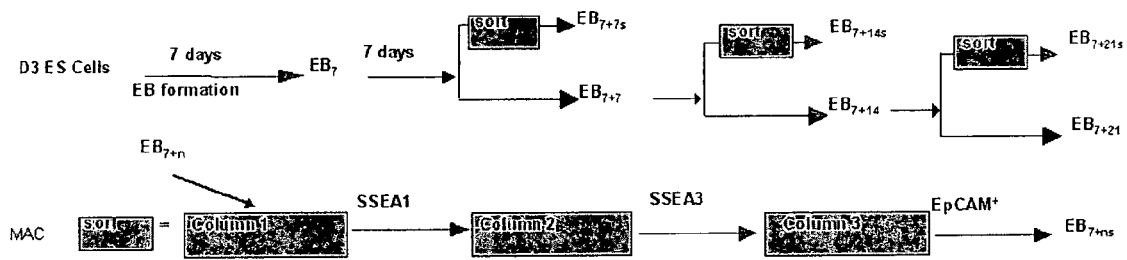

Real-time quantitation of gene expression relative to undifferentiated D3 mES cells

|  | EpCAM | sox17 | oct4 | pdx1 | ngn3 | peptide YY | ins1 |
|---|---|---|---|---|---|---|---|
| $EB_{7+0}$ | -1.97 | 181.02 | -2.43 | 2.93 | -1.59 | 72.00 | 4.80 |
| $EB_{7+7}$ | -2.06 | 625.99 | -9.45 | 18.00 | -2.38 | 14.12 | -2.66 |
| $EB_{7+7s}$ | 3.78 | 1112.82 | -11.63 | 28.64 | -1.10 | 48.73 | 2.23 |
| $EB_{7+14}$ | 1.11 | 256.59 | -12.52 | 40.13 | 2.80 | 85.04 | 9.62 |
| $EB_{7+14s}$ | 6.53 | 1087.40 | -69.87 | 123.35 | -1.06 | 77.89 | 4.97 |
| $EB_{7+21}$ | 1.09 | 1024.00 | -739.29 | 16.11 | 5.66 | 28.71 | 1.33 |
| $EB_{7+21s}$ | 5.17 | 951.02 | -403.57 | 174.05 | 1.01 | 82.90 | 3.55 |
| AP | 19.20 | 675.59 | -1120.56 | 2998.45 | 5.24 | 18776.88 | 430802.37 |

$EB_{n1+n2}$=D3 embryoid body, n1=days in suspension, n2=days on gelatin, s=MAC sorted; AP=Adult Pancreas; numbers are reported as the mean of three technical replicates

FIG 7

DIFFERENTIATION OF STEM CELLS TO ENDODERM AND PANCREATIC LINEAGE

CROSS-REFERENCE TO RELATED APPLICATIONS

This application claims priority from provisional patent application No. 60/559,209 filed Apr. 1, 2004.

STATEMENT REGARDING FEDERALLY SPONSORED RESEARCH OR DEVELOPMENT

To be determined.

BACKGROUND OF THE INVENTION

Type I diabetes is an autoimmune disease of humans caused by destruction of pancreatic islet beta cells. At present the disease is irreversible, although its symptoms are controlled by the administration of exogenous insulin. Type I diabetes is one of the most common autoimmune diseases in human populations and is a major public health concern.

It has previously been found that transplantation of a whole pancreas or of isolated islet cells is an effective treatment for Type I diabetes to restore insulin independence, when combined with immunosuppressive therapy. The success of existing therapies with isolated islets from human cadaver donors is a proof in principle that a cell-based therapy for human diabetes can be successful. However, the lack of available organs or islet cells has restricted this therapy only to very selected patients. The amount of islet cells which can be harvested from human cadavers is extremely limited. Therefore, a technology that is capable of producing significant quantities of islet cells would be highly desirable with regard to potential therapies for this disease.

Primate and human embryonic stem cells have been isolated and proliferated in culture. Embryonic stem cells are stem cells that can be maintained indefinitely through self-renewal and proliferation in culture, but which also retain the ability to differentiate spontaneously into cells of many different lineages. Under nonselective conditions, it has been previously demonstrated that a wide variety of stem cells, including mouse and human embryonic stem cells, will differentiate spontaneously into cells of many lineages including the pancreatic lineage. It has been previously shown that such differentiated cells can express the pancreatic duodenal homeobox 1 (PDX 1) gene, a transcription factor specifying the pancreatic lineage and can also express the insulin hormone. However, without selective conditions, stem cells will spontaneously differentiate into a wide variety of different lineages and only a small proportion of the cells will be differentiated towards any particular lineage. In addition, unselected stem cell populations are tumorigenic, meaning that they will generate non-malignant tumors, known as teratomas, in immunodeficient animals in that same way that undifferentiated cells ES cells will.

BRIEF SUMMARY OF THE INVENTION

The present invention is directed toward methods to direct the differentiation of human embryonic stem cells to the lineage of pancreatic islet cells.

The present invention is also directed toward methods for deriving endoderm enriched populations of cells that do not form teratomas when transplanted into hosts.

The present invention is also directed toward cultures of cells that have committed to the endoderm lineage, can differentiate further into pancreatic islet cells, and do not form teratomas upon transplant.

The present invention also is believed to be the first demonstration that cell based selection can be used in cell cultures derived from human embryonic stem cells, to remove the tumorigenic potential from the cultures without the use of exogenous genes inserted into the cells.

It is a feature of the present invention that it enables the production of endoderm and pancreatic cells in large numbers while overcoming one of the largest hurdles to potential use of stem cell derived cells for transplant, the tumorigenic character of undifferentiated stem cell.

Other object features and advantages of the present invention will become apparent from the following specification.

BRIEF DESCRIPTION OF THE SEVERAL VIEWS OF THE DRAWINGS

FIG. 7 is a chart and table showing the characteristics of islet precursors from murine ES cells sorted using the enrichment processes described below.

DETAILED DESCRIPTION OF THE INVENTION

Figure 1:
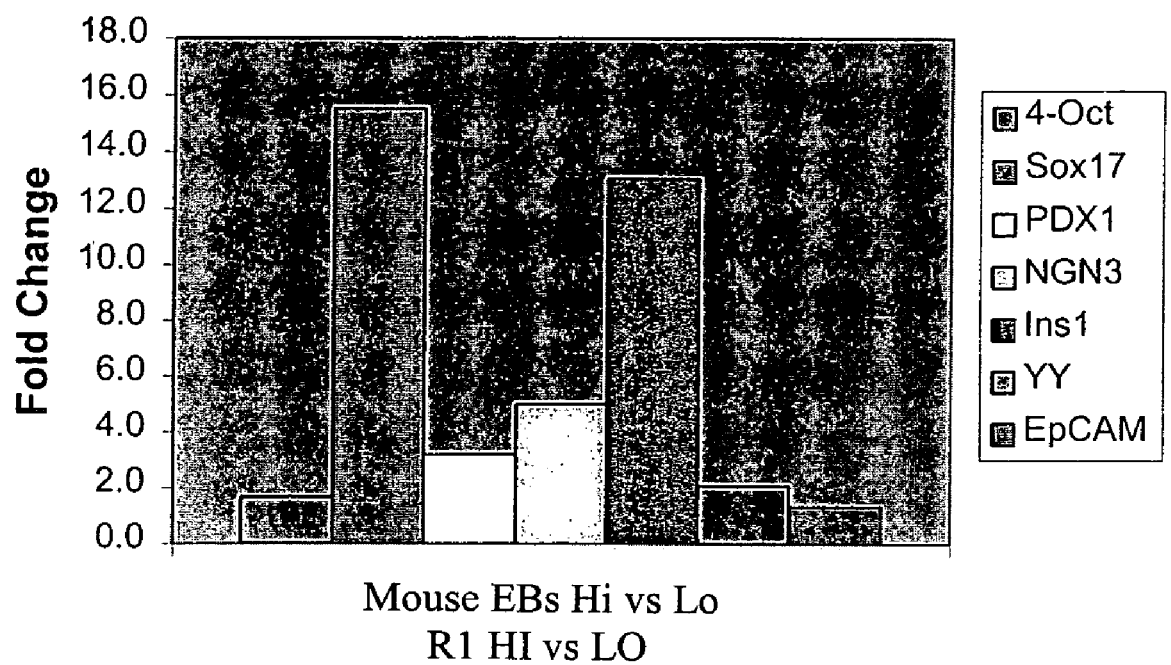
FIG. 1 is a graphical illustration of some of the results from the examples below showing the characteristics of sorted embryoid bodies.

Techniques are described here for guiding the differentiation of primate and human embryonic stem cells such that the population of cells is enriched for cells which are committed to an endoderm fate, including cells dedicated to a pancreatic lineage. In other words, the process results in a mixture of cells that are enriched for the percentage of pancreatic progenitor cells. Three separate techniques are described here, each of which acts independently to enrich the percentage of pancreatic progenitor cells produced by the culture. In total, the three methods represent the best techniques known so far to enrich differentiated cell cultures produced from human embryonic stem cells to have the highest possible contribution of pancreatic progenitor cells. It is also taught here that sorting cells to remove undifferentiated cells by binding cell surface antigens, using methods that do not involve inserted exogenous genes, is effective within this cell population to eliminate teratoma formation, a highly important attribute for any cell population which might someday be introduced into human patients. It is believed that this might be the first demonstration that the tumorigenic capability of undifferentiated ES cells can be effectively removed from ES cell differentiated progeny by intelligent choice of selection criteria.

In one of our standard methods for producing pancreatic progenitor cells from human embryonic stem cells, we first differentiate embryonic stem cells in vitro by putting single undifferentiated ES cells into suspension cultures. In the suspension cultures the ES cells aggregate and form two layered structures called embryoid bodies (EBs), which resemble pre-implantation stage embryos and which possess cells partially committed to the three embryonic germ layers, mesoderm, ectoderm and endoderm. Based on a study of normal embryos, early embryonic inductive interactions that promote diverse tissue differentiation events begin at this stage of development. Many of these important tissue inductive interactions may occur at this stage and in embryoid bodies. After 7-14 days of suspension culture, EBs are plated onto a tissue culture substrate and are allowed to proliferate and differentiate further under routine tissue culture conditions. Considerable differentiation of some neural and mesenchymal cell types happens spontaneously at this stage, requiring little further intervention. The appearance of embryonic endoderm cells giving rise to the pancreatic lineage, however, appears to be more complex, involving numerous and multifaceted interactions which have been only partially defined by classical developmental studies.

We have developed three interventions that increase the percentage of pancreatic lineage cells in a stem cell culture undergoing differentiation. The first method involves a selection of EBs that have greater potential for developing into definitive endoderm cells, the lineage from which pancreatic cells derive. The second enrichment methodology involves the use of a medium using a growth-enhancing factor which promotes the growth of pancreatic cell types. The third technique involves the three-tier approach of both positive and negative selection to both eliminate unwanted cells and to select for cells of the desired lineage. The three techniques may be used together or independently to increase the percentage of cells in a culture differentiating into the pancreatic lineage.

Some of the procedures described below were first performed with mouse ES cells. These procedures can be readily adapted for use with human ES cells. While the derivation and some of the cell surface markers of mouse ES cells differ from that of human ES cells, the cell selection methods described below are equally applicable to human ES cells, with the only significant change being that the markers used for selection must be altered to be those appropriate for human cells as opposed to murine cells. For example, the selection criteria for selection against undifferentiated ES cells is based on the cell surface antigen SSEA-1 in mouse ES cells and SSEA¾ markers in human ES cells. Similarly, to remove visceral yolk sac (VYS) cells from the culture, one selects against expression of SSEA-3 in mouse cell cultures and against expression of SSEA-1 in human cell cultures. Endothelial cells of both mouse and human will express the epithelial cell adhesion molecule (EpCAM), the expression of which can be used for positive selection to identify murine or human cells which are committed to the endothelial lineage.

For performing these selections, an instrument capable of selecting larger particles in general, and whole EBs in particular, is desirable. One such instrument is the COPAS instrument (Union Biometrica, Inc.), which operates on principles similar to those of a fluorescence-activated cell sorter (FACS) machine, but which accepts cellular particles of larger size. Any instrument capable of sorting cellular aggregates should be adaptable for use in the present methodology. Magnetic activated cell sorting (MACS) has also be successfully adapted for use in this kind of cell sorting procedures as well.

Another attribute of the processes described here is the finding that the tumorigenic tendency of stem cell cultures can be removed effectively solely by selection. When injected into immunocompromised mice, ES cells will form teratomas, which are non-malignant growths or tumors made up of many different tissue types in a poorly organized structure. While the generation of teratomas is not thought to be life-threatening to the host, the teratomas can be large, unsightly and wasteful of metabolic energy to the host. A characterization of the teratomas formed by human ES cells is found in Gertow et al., *Stem Cells and Development*, 13:421-435 (2004). If human ES cells are to be used ultimately for transplantation of cells or tissues into human patients, the cells which are so introduced would presumably be preferred to be free of tumorigenic capacity. In the art, the main techniques which have been taught to eliminate this capability are based on inserting exogenous gene constructs into ES cells and then selecting for differentiated cells based on expression characteristics of the introduced genes. However, the use of exogenous genes inserted into human ES cell cultures carries another set of safety concerns that are best avoided. Here it is taught, perhaps for the first time, that cell selection based on cell surface markers is sufficient at a practical level to produce a stem cell derived cell culture that is not tumorigenic and does not form teratomas. As the risk of redundancy, and to avoid misunderstanding, the use of the phrase tumorigenic is intended to apply to the teratoma-forming characteristics of undifferentiated human ES cells and is not intended to imply malignancy of any kind since ES cells do not produce malignancies when injected into mice. The removal of the tumorigenic trait simply by selection is another important step in the progression of stem cell derived from laboratory model to useful human therapy.

EXAMPLES

General Culture Conditions:

Undifferentiated murine ES cells were grown in DMEM-High Glucose medium supplemented with 15% FCS, L-glutamine, NEAA (non-essential amino acids), mercaptoethanol (MES medium) and LIF on irradiated feeder cells as described previously (Kahan et al., 2003). To produce EBs, ES cell monolayers were treated with 2 mM EDTA with 2% chicken serum for 15 min. Cells were resuspended in MES medium and filtered though a 20 µm Nitex filter to obtain a single cell suspension. $2 \times 10^6$ cells were placed in a siliconized non-tissue culture P60 dish in 5 ml MES medium in 10% $CO_2$. Cultures were renewed daily and split into larger dishes to prevent medium acidification. 7-day EBs were collected, counted and placed at a density of 30-50 EBs in 24 well plates containing 13 mm glass gelatin-coated coverslips for immunohistochemical staining, or in proportionately larger numbers in gelatinized tissue culture dishes for other analyses including quantitative PCR (QPCR). EBs were plated in DMEM-high glucose medium with 10% FCS in 5% $CO_2$.

Conditions for the culturing of human ES cells were similar, except that the undifferentiated cells were maintained on feeder cells in DMEM/F12 medium supplemented with 15% Serum Replacement (SR), NEAA, L-glutamine, mercaptoethanol and bFGF (4 ng/ml). Human EBs were initiated from intact colonies of ES cells, rather that from single cells, by lightly treating cultures with dipase and collagenase just until the colonies loosened. The EBs were maintained in suspension in the previous medium which was supplemented with 15% fetal calf serum (FCS) and which was lacking bFGF. After fourteen days of suspension culture, the EBs were plated in DMEM/F12 medium containing 10% FCS in 5% $CO_2$.

1: Selection for Intact EBs Expressing a Cell Surface Antigen, Stage-Specific Embryonic Antigen-3 (SSEA-3).

Not all ES aggregates successfully mature into EBs with an outside cell layer of fully differentiated visceral yolk sac (VYS) cells, which express SSEA-3. After briefly incubating live EBs with a monoclonal anti-SSEA-3 antibody and a fluorescently tagged secondary antibody, high-expressers in the population were separated using a COPAS instrument (Union Biometrica, Inc.), which operates on principles similar to those of a fluorescence-activated cell sorter (FACS) machine. However, the COPAS instrument, which can be thought of as a large particle cell sorter, has a much larger aperture and can sort entities on the size order of whole pancreatic islets and entire *C. elegans* worms. EBs selected by the machine were sorted into tissue culture wells, cultured further to allow differentiation and analyzed for expression of pancreatic markers.

SSEA-3 Staining:

The 7 day EBs were incubated for 15 min at 40° C. with monoclonal anti-SSEA-3 ascites (Developmental Studies Hybridoma Bank, U Iowa) diluted 1:50 in DMEM with 10% FCS, and then rinsed with a 20-50 fold excess of cold DMEM with 10% FCS. Next, the EBs were incubated with secondary antibody (Alexa-fluor 488 goat anti-rat IgM (1:1000) (Molecular Probes)) in DMEM with 10% FCS for 15 min at 40° C. and rinsed as before. For COPAS sorting, stained EBs were suspended in cold PBS containing Ca++, Mg++ and 1% FCS and sorted into wells containing medium supplemented with gentamycin.

Results:

After differentiating for 21 additional days following sorting, cultures initiated using the highest 5-10% SSEA-3 EB expressers showed many more cells (estimated 10 fold) staining for YY, a marker of early pancreatic cells, than did unsorted cultures containing mainly SSEA-3 negative EBs. FIG. 1 illustrates that the SSEA-3 high cells, sorted by the large particle cell sorter contained more endoderm transcripts (Sox17 and Pdx1) and indicators of islet differentiation (NGN3 and insulin(Ins1)) than did SSEA-3 negative or low cells. These results indicate successful enrichment of the culture for cells of the endoderm and pancreatic lineage.

2: Treatment of Differentiating Cells with Medium Supplemented with FGF10.

Fibroblast growth factor 10 (FGF10) has been reported in the literature to be necessary for normal development of the pancreas and may act by promoting proliferation of early pancreatic precursor cells (Bhushan, et al., 2001.) FGF10 is expressed in the mesenchyme surrounding the early pancreatic epithelium in mouse and human embryos. It was decided to explore the effect of this growth factor on differentiation of ES cell cultures.

Culture in Medium Supplemented with FGF10:

The EBs were developed as described above and plated on day 7 in DMEM-High glucose with 10% FCS. Two days later, this medium was replaced by DMEM-High glucose with 1% FCS medium containing 50 ng/ml FGF10. Medium containing FGF10 was renewed daily for 5-19 additional days, until the cells are analyzed for pancreatic markers by immunofluorescence and/or quantitative PCR methods (QPCR).

Figure 2:
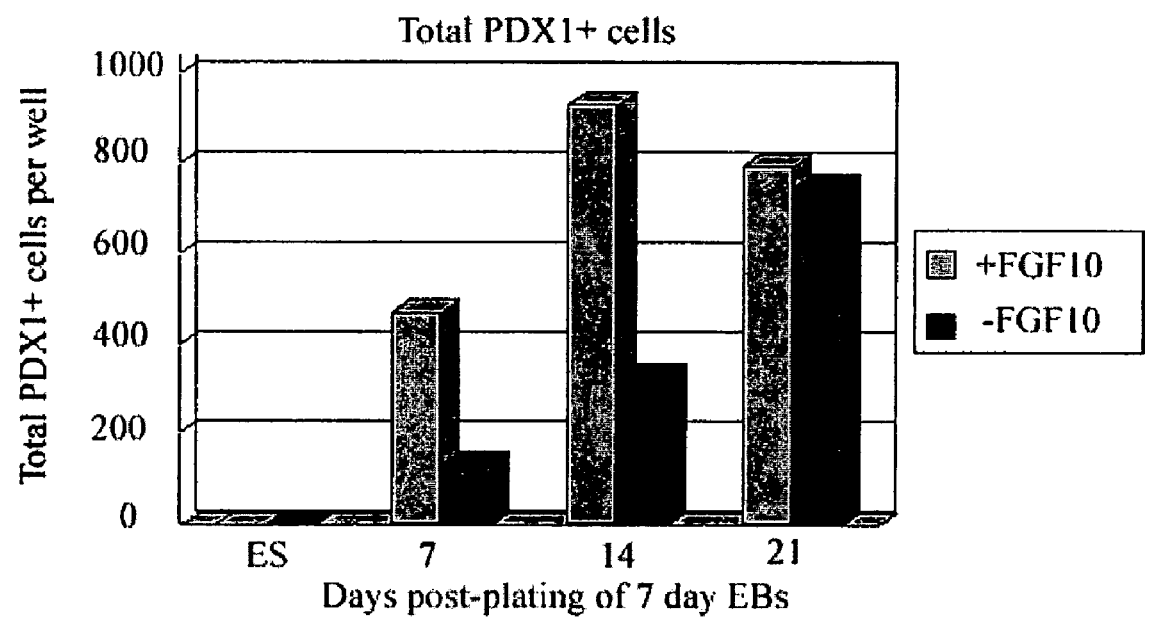
FIG. 2 is another graphical presentation of some of the results from the examples below showing proportions of cells which are positive for PDX1.
Figure 3:
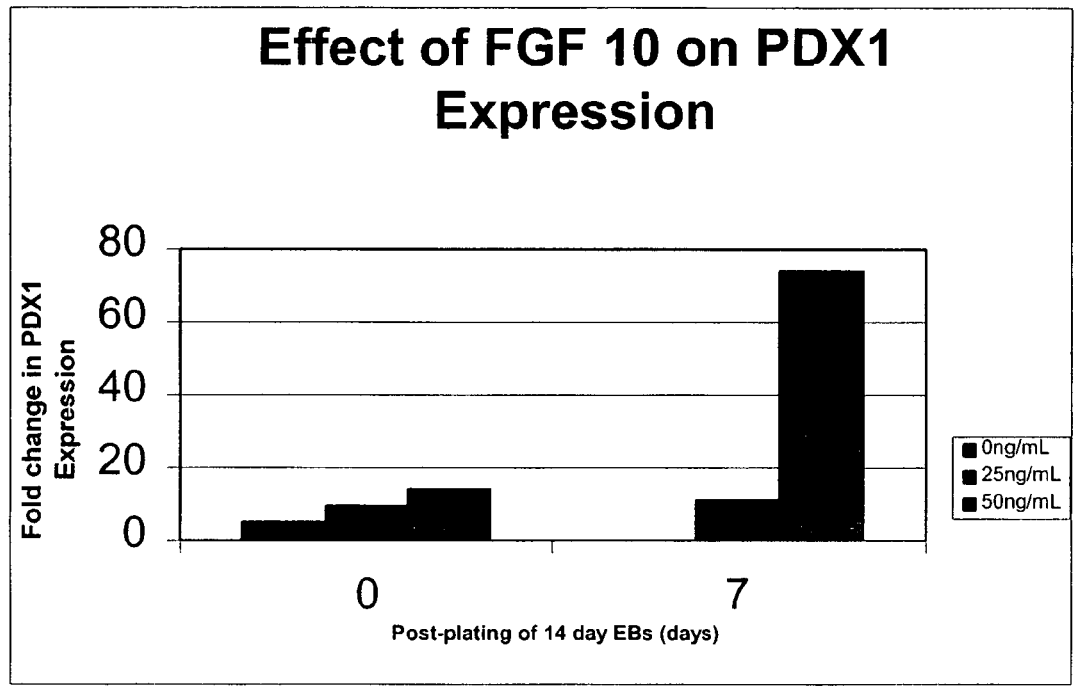
FIG. 3 is another graphical illustration of results illustrating the effect of the use of FGF10 on PDX1 expression in cell cultures.

Results:

Analysis of the resulting fluorescent and QPCR tests revealed a significant enhancement of PDX1 expressing pancreatic progenitors. Table 1 below shows supporting QPCR data indicating a 5 and 2.5 fold enrichment of pdx1 transcripts at 7 and 14 days after plating, as compared respectively to untreated cells. Similarly, there was a 2.5 fold increase of insulin transcripts by 14 days after plating compared to cells grown in the absence of FGF10. FGF10 used at a concentration of at least 50 ng/ml was effective. FIG. 2 illustrates an increased number of cells staining for PDX1 (2 to 3 fold more) after 12 days growth in FGF10 supplemented medium. Table 1 shows supporting QPCR data. FIG. 3 illustrates QPCR data exhibiting enhanced pdx1 transcript abundance in FGF 10 treated cell cultures. Relative to undifferentiated human ES cells, differentiated derivatives exposed to 50 ng/ml FGF10 exhibited 70 fold more pdx1 transcript mRNA. The FGF10 effect was more pronounced when cells were exposed to the FGF10 in the phase following EB culture.

TABLE 1

Increased pdx1 expression in FGF10-treated cells. Average fold change in expression relative to undifferentiated D3 mES cells using quantitative real-time PCR

| | EpCAM | sox17 | oct4 | pdx1 | ngn3 | peptide YY | ins1 |
|---|---|---|---|---|---|---|---|
| $EB_{7+7}$ | −2.06 | 625.99 | −9.45 | 13.00 | 2.38 | 14.12 | −2.66 |
| $EB_{7+7\ FGF10}$ | −1.11 | 294.75 | −7.21 | 83.48 | 1.60 | 15.17 | −1.71 |
| $EB_{7+14}$ | 1.11 | 256.59 | −12.52 | 40.13 | 2.80 | 85.04 | 9.62 |
| $EB_{7+14\ FGF10}$ | 2.19 | 232.32 | −8.11 | 110.41 | 2.49 | −0.01 | 25.11 |
| $EB_{7+21}$ | 1.09 | 1024.00 | −739.29 | 16.11 | 5.66 | 28.71 | 1.33 |
| $EB_{7+21\ FGF10}$ | −2.73 | 170.86 | −8.24 | 19.38 | −1.06 | 17.84 | −3.09 |

$EB_{n1 + n2}$ = D3 embryoid body,
n1 = days in suspension,
n2 = days on gelatin;
FGF10 = 50 ng/ml;
AP = Adult Pancreas; number are reported as the mean of three technical replicates 3: Enrichment of Pancreatic Precursor Cells and Reduction in Teratogenicity Using Magnetic Activated Cell Sorting (MACS) Separation.

Previously, it has been shown that ES cell progeny express the pancreatic duodenal homeobox (PDX1, IPF1), an essential pancreatic transription factor. It is now reported here that ES cell derived cells expressing PDX1 were found to reside in discrete loci within the ES cell differentiation cultures among sheets of epithelial-like cells that expressed the cell surface antigen, epithelial cell adhesion molecule (EpCAM). While the majority of EpCAM expressing cells were PDX1 negative, all of the PDX1-expressing cells also co-expressed EpCAM. Significantly, many of the other cell types within these cultures, including neural and mesenchymal cells, did not stain for EpCAM. Therefore, we reasoned that by selecting for EpCAM positive cells, it might be possible to enhance the relative proportion of the PDX1 positive cells. However, some undifferentiated ES cells and visceral yolk sac (VYS) cells also co-stained for EpCAM. The strategy devised was to first remove undifferentiated ES cells, based on their exclusive expression of the cell surface antigen SSEA-1 (in mouse ES cells) and SSEA3⁄4 (in human ES cells). Then the VYS cells were removed, based on their exclusive expression of SSEA-3 in mouse cultures and SSEA-1 in human cultures.

Finally, an endoderm population expressing EpCAM was selectively isolated using a positive selection for EpCAM positive cells. The MACS method used is based on attaching magnetic beads to a secondary antibody, and then passing the cells through a separation column that is placed in a strong permanent magnet. The magnetically labeled cells were retained in the column and separated from the unlabeled cells, which pass through. After removing the column from the magnetic field, the retained fraction was eluted. Both negative and positive selection strategies are possible, depending on whether one keeps the retained cells or the pass-through cells.

The MACS Separation Protocol is a detailed protocol described below, outlining the steps involved in the process for mouse ES cells using two negative selection columns (using SSEA1 and then SSEA3 primary antibodies) to remove ES and VYS cells, and finally a third positive column selection for EpCAM expression. For human ES cell cultures, the three separation strategy is similar, except that the first negative selection is with SSEA¾ to remove undifferentiated human ES cells, followed by removal of VYS cells by SSEA1 negative selection, and then by the EpCAM positive selection step.

MACS Separation Protocol

Cell Preparation for First Negative Separation

The procedure began with rinsing 3 P60 plates $EB_{7+n}$ with PBS, 2×. Then we incubated the plates for 15 min in 1.5 ml 2 mM EDTA and aspirated the EDTA. We then added 1.5 ml 0.05% trypsin for 5 min, 37° C., followed by adding 1.5 ml DMEM/HEPES+10% FCS and resuspending cells gently. We then added additional DMEM+10% FCS to make total of 10-15 ml. The cells were then filtered through a 40 µm filter into a 50 ml tube and re-filtered with 20 µm Nitex filter. The filtrate was diluted 1:5 with Toluidine Blue (TB) and the cells were counted (50 µl+150 µl+50 µl TB). We added $2 \times 10^7$ cells to 2 15 ml tubes and centrifuge tubes in clinical centrifuge for 3 min, speed #5. We then resuspended each pellet in 100 µl DMEM/HEPES+10% FCS containing SSEA-1 antibody and incubated in refrigeration (4-8° C.) for 15 min. Then 5 ml cold DMEM/HEPES+10% FCS was added per tube and centrifuged 3 min, 21° C. Then the supernatant was completely removed. The cells were resuspended in 160 µl DMEM/HEPES+10% FCS/tube and 40 µl rat anti-mouse IgM Magnetic beads were added to each tube. This mixture was mixed well and incubated in refrigeration (4-8° C.) for 15 min. To this was added 5 ml cold DMEM/HEPES+10% FCS/tube followed by centrifuging for 3 min, 21° C. The supernatant was removed completely. The each pellet was resuspended in 0.5 ml cold degassed DMEM/HEPES+10% FCS. To do this, about 40 ml DMEM/HEPES+10% FCS was degassed for 10 min at RT using vacuum followed by chilling the mixture.

First Negative Selection

To prepare the instrument the magnet was attached to the stand and the LD column was placed in magnet with collection tube underneath. Each column was thoroughly washed, by applying 2 ml of cold degassed DMEM/HEPES with 10% FCS and letting the medium run through each column. The medium was transferred to sterile 15 ml collection tube in ice. Then cells were added to medium followed by adding 1 ml cells to LD column and collecting the effluent. We then washed the column with 2×1 ml degassed medium and collected total effluent as the depleted fraction. We then removed 10 µl cells and diluted them 1:10 to count (10 µl+40 µl+50 µl TB), followed by centrifugation at 3 min, 21° C.

Cell Preparation for Second Negative Separation

Aliquots of cells from the previous procedure were suspended in 160-240 µl DMEM/HEPES+10% FCS (80 µl/$10^7$ cells). To that we added 40-60 µl goat anti-rat IgG magnetic beads (20 µl/$10^7$ cells). This combination was mixed well and incubated in refrigeration (4-8° C.) for 15 min. Then 5 ml DMEM/HEPES+10% FCS was added and the mixture centrifuged for 3 min, 21° C., followed by removal of the supernatant completely. The pellet was resuspended in 1 ml cold degassed DMEM/HEPES+10% FCS.

Second Negative Separation Column

The second LD column was washed by applying 2 ml of cold degassed DMEM/HEPES+10% FCS and letting it run through. The medium was transferred to sterile 15 ml collection tube in ice. Then we applied the cells to the LD column and collected the effluent. We washed the column with 2×1 ml degassed medium and collected the total effluent as the depleted fraction. The cells were then counted and diluted 1:4=10 µl+10 µl+20 µl TB. The mixture was then centrifuged for 3 min, 21° C.

Cell Preparation for Positive Separation

The pellet from the previous procedure was resuspended in 100 µl DMEM/HEPES+10% FCS containing anti-EpCAM antibody and incubated in refrigeration (4-8° C.) for 15 min. To this was added 5 ml cold DMEM/HEPES+10% FCS and the combination was centrifuged 3 min, 21° C. The supernatant was removed. The cells were resuspended in 80-160 µl DMEM/HEPES+10% FCS to which was added 20-40 µl goat anti-rat IgG magnetic beads. The combination was mixed well and incubated in refrigeration (4-8° C.) for 15 min. The we added 5 ml cold DMEM/HEPES+10% FCS and centrifuged 3 min, 21° C., followed by removal of the supernatant completely. The cells were resuspended in 1 ml cold degassed DMEM/HEPES+10% FCS.

Positive Separation Column

We first washed the LS column by applying 3 ml cold degassed DMEM/HEPES+10% FCS and letting it run through. The medium was transferred to 15 ml collection tube. We applied the cells to LS column and collected the effluent. We washed the column with 3×3 ml DMEM/HEPES+10% FCS and let the entire 3 ml pass through before adding more. The LS column was removed and placed in a sterile 15 ml centrifuge tube. To the column we added 5 ml DMEM/HEPES+10% FCS and firmly flushed out the attached, positive fraction using plunger supplied with the column. The cells were centrifuged for 3 min, 21° C. and resuspended in 1-2 ml MES/HEPES medium+gentamycin. We then performed a cell count on collected cells and diluted the cells 1:2 with TB. The cells were plate at 1-$2 \times 10^5$ cells/well in 24 well plates.

The antibody dilutions were as follows:

For negative selection: SSEA-3: Add 4 µl to 200 µl to dilute 1:50 using ascites-unk to a final dilution of 1:50. SSEA-1: Add 40 µl to 200 µl to dilute 1:5 to dilute a stock of 500 µg/ml to a final of 10 µg/ml.

For positive selection: EpCAM: Add 2 µl to 100 µl for a dilution of 1:50 to dilute a stock of 500 µg/ml to 10 µg/ml.

Figure 5:
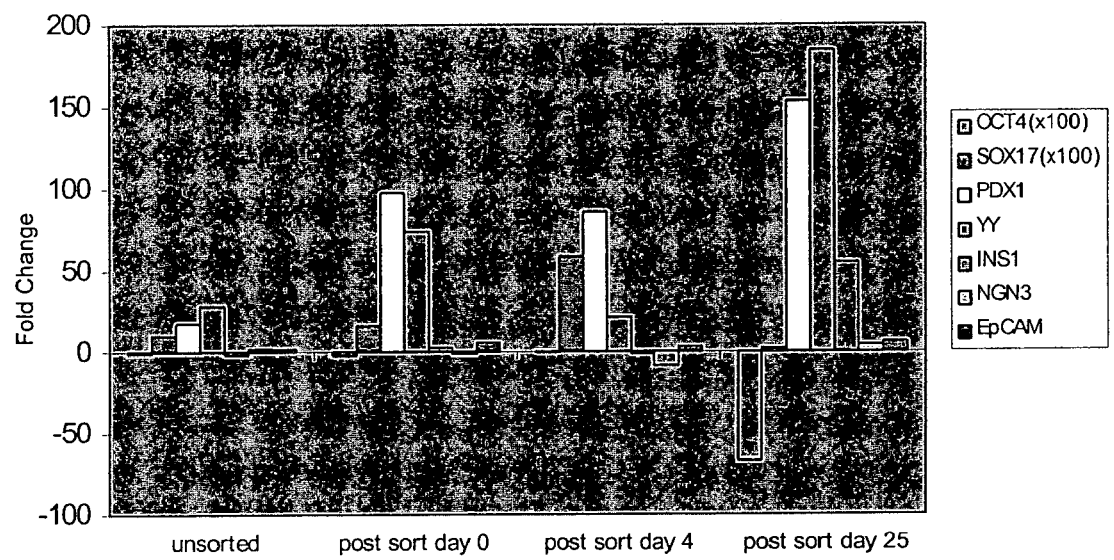
FIG. 5 is a graphical illustration of the results obtained characterizing sorted cells.

To test whether EpCAM+cells (~98% pure) selected by the MACS sorting strategy were enhanced for endoderm and pancreatic lineages, QPCR analyses were performed on cells immediately following sorting and also after 4 days of growth in DMEM+15% SR and FGF10 (post sort, day 4; FIG. 5). At this time, further enhancement of pancreatic differentiation of post-sorted cells was achieved by switching cultures to conditions representing a modification of the pancreatic progenitor differentiation protocol of Bonner-Weir et al, (2001), consisting of a Matrigel substrate and DMEM/F12 medium containing BSA, ITS, beta-mercaptoethanol, NEAA, L-glutamine, nicotinamide, exendin 4 and FGF 10. Post-sorted cells were further analyzed by QPCR and IHC after 21 days in differentiation medium (post-sort day 25, FIG. 5).

To test whether the sorting strategy reduces teratoma formation after growth of ES cells in vivo, we transplanted either undifferentiated mouse ES cells, or differentiated, unsorted ES cell-derived cells or differentiated, freshly sorted ES cell progeny into immunodeficient (NOD-SCID) mice. Graded numbers of cells were injected under the renal capsule or subcutaneously. Animals were monitored for tumor formation for up to 10 weeks, subcutaneous tumors were measured every 3 days, and histology was performed on kidneys of injected animals.

Figure 4:
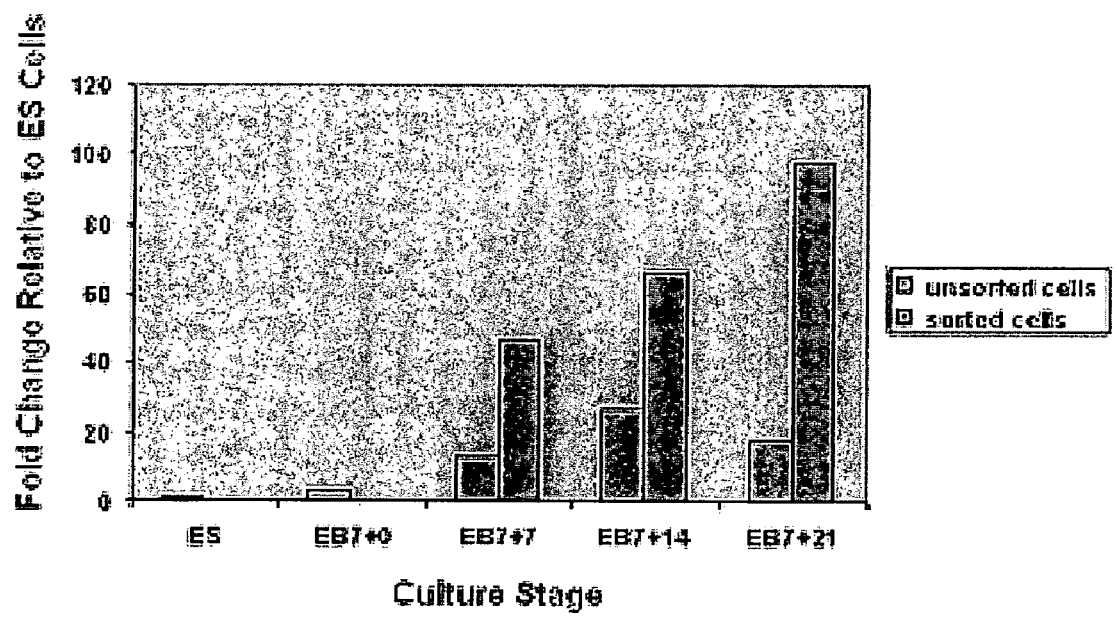
FIG. 4 is another graphical illustration of data showing QPCR analysis of Pdx1 transcription.

Results:

FIG. 4 and FIG. 7 show enrichment of PDX1-expressing cells in sorted populations as assayed by QPCR. In FIG. 4, mouse ES cells were cultured to different stages as indicated on the x-axis and then sorted for EpCAM+ cells as noted above. Pdx1 gene expression was assessed by QPCR and compared to undifferentiated ES cells (column 1 and normalized to 1.0 fold). All data are also normalized to GAPDH control levels and data points represent biological duplicate or triplicate samples. These data show that without sorting, pdx1 transcripts increase only slightly over time as the cells differentiate in culture and eventually pdx1 expression plateaus, indicating the absence of further relative increase in pdx1 transcription in later stage cultures. In contrast, pdx1 transcripts continue to accumulate over time in EpCAM+ cells. Ultimately, sorted cells demonstrate a >95-fold enrichment of pdx1 gene expression compared to undifferentiated ES cells and a 4-5 fold enrichment compared to unsorted cells. FIG. 7 shows the results of another sorting experiment which demonstrates a significant increase in endoderm markers Sox17, and reduction in Oct 4, an undifferentiated stem cell marker, over time that is enhanced using this sorting strategy. Again, pdx1 expression in EpCAM+ sorted cells was increased 3-10 fold over that in unsorted populations.

EpCAM+ cells that were approximately 98% pure were placed in culture medium as indicated above containing 15% SR (serum replacer) and FGF10 for 4 days, followed by culture for an additional 21 days of culture in serum free medium containing nicotinamide, exendin4, and FGF10. FIG. 5 demonstrates that this differentiation protocol for post-sorted cells results in a progressive trend away from undifferentiated cells and endoderm towards more differentiated islet phenotypes. More specifically, and as shown in a previous experiment, sorting results in a significant enrichment of pdx1 and YY transcripts (post-sort day 0 vs unsorted). After 4 days in FGF10 supplemented medium, cultures exhibited a ~300 fold increase in Sox17 transcription (post-sort day 4 vs. post-sort day0). This was accompanied by a ~4-5 fold increase in total cell number over 4 days without a reduction in pdx1 or Epcam transcription that was likely due to proliferation. Subsequent culture of this expanded population in serum free medium for 21 days (up to 25 days post-sorting) as indicated in the methods resulted in a dramatic decrease in the expression of undifferentiated stem cell markers (Oct 4), indicating committed differentiation of undifferentiated stem cells. In addition, there was a maturation of endoderm, based on the reduction in Sox 17 transcription. Simultaneously, we observed a consistent and significant increase in the levels of pancreatic marker gene expression (Pdx1, YY and Insulin). Under these differentiation conditions, cells altered their morphology in a striking way, coalescing and eventually forming tubule-like or duct-like structures. Overall, compared to unsorted cells, the sorting scheme and culture protocol to induce further expansion and differentiation resulted in an increase in pancreatic precursors cells, an estimated 12-fold from 0.07% of the total population to 0.9% of the total population. Furthermore, it is estimated that the protocol can successfully produce a 50-fold increase in insulin expressing cells. Such changes in gene expression and morphology mirror many of the cellular and molecular changes that occur in the embryo during pancreaticogenesis.

Figure 6:
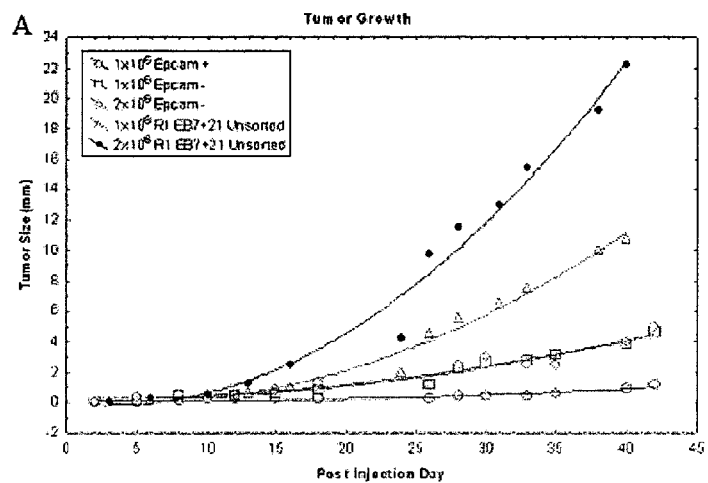
FIG. 6 is a graphical illustration showing the tumorigenic capability of sorted cells.

Based on the significant reduction in Oct4 expression, we hypothesized that EpCAM+ cells would be less likely to form teratomas. Therefore, we designed an experiment to test this hypothesis. First, we transplanted $0.5 \times 10^6$ undifferentiated murine ES cells or unsorted populations of differentiated murine ES cells under the kidney capsule of immunodeficient 8 week-old NOD-SCID mice. Kidneys were harvested 3 weeks after injection. All such animals developed grossly visible tumors. In contrast, animals injected with $0.5 \times 10^6$ SSEA1 negative, SSEA3 negative, and EpCAM positive cells did not develop teratomas either grossly or histologically (0 of 5 animals). Therefore, MACS-sorted cells do not generate teratomas when injected under the kidney capsule in immunodeficient mice. FIG. 6 shows another experiment in which cells were inoculated subcutaneously. This experiment also included another control cell population, SSEA1-, SSEA3-, and EpCAM-sorted cell populations and examined growth for up to 10 weeks. In the subcutaneous location, undifferentiated ES cell inoculated into the mice rapidly grew into large teratomas (>10 mm), and differentiated sorted cells also readily formed tumors (FIG. 6). Importantly, undifferentiated ES cells also generally form teratomas in immuno-competent mice (data not shown). Strikingly, EpCAM+ differentiated cells that had been previously sorted by the three-stage strategy failed to form tumors (FIG. 6). Stable nodules less than 3 mm in size formed in all cases of EpCAM+ sorted cell injections, remaining unchanged up to 10 weeks after inoculation. Histological analysis of the nodules showed a prevalence of glandular structures, suggestive of endoderm derivatives. The multiple varied derivatives of other germ layers typically seen in teratomas were not present in the nodules. Although sorted cell populations did not form teratomas in vivo, cells survived and proliferated in vitro under specific conditions identified in this application, indicating that death or apoptosis of the sorted population was not the reason for lack of teratoma formation. It also indicates that conditions for expansion of the cells in vitro have been devised while simultaneously reducing the tumorigenicity of the resulting cell populations.

All of the three methodologies recited above resulted in increasing the proportion of cells directed to endoderm and the pancreatic lineage from initially undifferentiated stem cell cultures. In particular, the MACS sorting strategy both enhanced pancreatic differentiation and reduced tumorigenicity of differentiated ES cell derivatives by removing residual undifferentiated ES cells. Thus, EcCAM positive cells selected by the MACS sorting scheme, in addition to providing the ability to enrich for endoderm and pancreatic lineages, are less tumorigenic, an important attribute for eventual clinical therapeutic applications. This is believed to be the first demonstration or reduced or eliminated tumorigenic capacity for ES cell progeny that does not involve the introduction of exogenous genes into the ES cells.

We claim:

1. A method to enrich a culture derived from human embryonic stem cells for cells of endoderm and pancreatic lineages, the method comprising the steps of
    (a) culturing intact colonies of human embryonic stem cells to form whole, intact embryoid bodies surrounded by visceral yolk sac (VYS) cells, wherein the human embryonic stem cells express Oct-4, surface stage-specific embryonic antigen-3/4 (SSEA 3/4) and epithelial cell adhesion molecule (EpCAM);

(b) culturing the embryoid bodies of step (a) under conditions that permit the embryoid body cells to differentiate into a cell population containing cells of the endoderm and pancreatic lineages;

(c) dispersing the cell population of step (b) into single cells;

(d) selecting against the expression of SSEA 3/4 positive cells to remove undifferentiated cells from the cells of step (c);

(e) selecting against the expression of SSEA-1 positive cells to remove VYS cells from the remaining cells of step (d); and (f) selecting from among the remaining cells of step (e) for the expression of EpCAM positive cells to enrich for cells of endoderm and pancreatic lineages.

2. The method of claim 1 wherein the selecting is performed by magnetic activated cell sorting.

3. A method to enrich a culture derived from human embryonic stem cells for cells of endoderm and pancreatic lineages, the method comprising the steps of (a) culturing intact colonies of human embryonic stem cells to form whole, intact embryoid bodies surrounded by visceral yolk sac (VYS) cells, wherein the human embryonic stem cells express Oct-4, surface stage-specific embryonic antigen-3/4 (SSEA 3/4) and epithelial cell adhesion molecule (EpCAM);

(b) culturing the embryoid bodies of step (a) under conditions that permit the embryoid body cells to differentiate into a cell population containing cells of the endoderm and pancreatic lineages;

(c) treating the cell population of step (b) with an effective amount of fibroblast growth factor 10 (FGFl0); and (d) dispersing the cell population of step (c) into single cells enriched for cells of endoderm and pancreatic lineages (e) selecting against the expression of SSEA-3/4 positive cells to remove undifferentiated stem cells from the cells of step (d);

(f) selecting against the expression of SSEA-1 positive cells to remove VYS cells from the cells of step (e); and (g) selecting from among the remaining cells of step (f) for the expression of EpCAM positive cells to enrich for cells of endoderm and pancreatic lineages.

4. The method of claim 3 wherein the selecting is performed by magnetic activated cell sorting.

5. An enrichment method for the creation of a stem cell derived cell population which does not have tumorigenic capability comprising the steps of (a) culturing intact colonies of human embryonic stem cells to form whole, intact embryoid bodies surrounded by visceral yolk sac (VYS) cells, wherein the human embryonic stem cells express Oct-4, surface stage-specific embryonic antigen-3/4 (SSEA 3/4) and epithelial cell adhesion molecule (EpCAM);

(b) culturing the embryoid bodies of step (a) under conditions that permit the embryoid body cells to differentiate into a cell population containing cells of the endoderm and pancreatic lineages;

(c) dispersing the cell population of step (b) into single cells;

(d) selecting against the expression of SSEA 3/4 positive cells to remove undifferentiated cells from the cells of step (c);

(e) selecting against the expression of SSEA-1 positive cells to remove VYS cells from the cells of step (d);and (f) selecting from among the remaining cells of step (e) for the expression of EpCAM positive cells, the resulting cells not forming teratomas when injected in immunocompromised mice.

6. The method of claim 5 wherein the selecting is performed by magnetic activated cell sorting.

7. A method to enrich a culture derived from human embryonic stem cells for cells of endoderm and pancreatic lineages, the method comprising the steps of (a) culturing intact colonies of the human embryonic stem cells to form whole, intact embryoid bodies surrounded by visceral yolk sac (VYS) cells, wherein the human embryonic stem cells express Oct-4, surface stage-specific embryonic antigen-3/4 (SSEA 3/4) and epithelial cell adhesion molecule (EpCAM);

(b) culturing the embryoid bodies of step (a) under conditions that permit the embryoid body cells to differentiate into a cell population containing cells of the endoderm and pancreatic lineages (c) treating the cell population of step (b) with an effective amount of fibroblast growth factor 10 (FGF 10) to enrich for cells of endoderm and pancreatic lineages;

(d) dispersing the cell population of step (c) into single cells;

(e) selecting against the expression of SSEA-3/4 positive cells to remove undifferentiated stem cells from the cells of step (d);

(f) selecting against the expression of SSEA-1 positive cells to remove VYS cells from the cells of step (e); and (g) selecting from among the remaining cells of step (f) for the expression of EpCAM positive cells to enrich for cells of endoderm and pancreatic lineages.

\* \* \* \* \*

UNITED STATES PATENT AND TRADEMARK OFFICE
CERTIFICATE OF CORRECTION

PATENT NO. : 7,585,672 B2 Page 1 of 1
APPLICATION NO. : 11/094902
DATED : September 8, 2009
INVENTOR(S) : Jon Odorico, Brenda Kahan and Nathan Treff It is certified that error appears in the above-identified patent and that said Letters Patent is hereby corrected as shown below:

Column 1, lines 13 - 15, should read:

--STATEMENT REGARDING FEDERALLY SPONSORED RESEARCH OR DEVELOPMENT

This invention was made with United States government support awarded by the following agency:

NIH DK61244

The United States government has certain rights in this invention.--

Signed and Sealed this

Tenth Day of November, 2009

David J. Kappos
*Director of the United States Patent and Trademark Office*